United States Patent [19]
Christidis et al.

[11] 3,983,114
[45] Sept. 28, 1976

[54] METHOD OF PREPARATION OF 6-AZA URACILE AND ITS O-DISILYL DERIVATIVE

[75] Inventors: Yani Christidis, Paris; Jean-Claude Vallejos, La Ciotat, both of France

[73] Assignee: Nobel Hoechst Chimie, Puteaux, France

[22] Filed: Oct. 24, 1975

[21] Appl. No.: 625,839

[30] Foreign Application Priority Data
Nov. 5, 1974  France .............................. 74.36754

[52] U.S. Cl. ........................................ 260/248 AS
[51] Int. Cl.² ...................................... C07D 253/06
[58] Field of Search .............................. 260/248 AS

[56] References Cited
UNITED STATES PATENTS
3,922,273   11/1975   Deutsch .............................. 260/248

Primary Examiner—John M. Ford
Attorney, Agent, or Firm—Karl W. Flocks

[57] ABSTRACT

A method of preparation of 6-aza uracile, comprising the steps of:

a. Cyclization of semi-carbazone of glyoxylic acid by heating this latter with an excess of a trialkyl-silylation agent taken as a solvent and isolating the resulting product, namely the O-disilylated derivative of 6-aza uracile (or di-3,5 (trialkylsiloxy)1,2,4 triazine) and b. subjection of the product resulting from step a) to an acid hydrolysis.

9 Claims, No Drawings

METHOD OF PREPARATION OF 6-AZA URACILE AND ITS O-DISILYL DERIVATIVE

The present invention relates to a method of preparation of 6-aza uracile and its O-disilyl derivative.

It is known to manufacture 6-aza uracile by cyclization of semi-carbazone of glyoxylic acid by means of an alkaline base, followed by liberation of the 6-aza uracile by an acid. Various alkaline cyclization agents have been proposed, such as aqueous NaOH, an alkaline alcoholate in an alcohol medium and ethylene-glycol, NaOH in an alkylene-glycol medium. The yields obtained in this cyclization are not generally very high.

In addition, the synthesis of 6-aza uridine, a compound possessing more pronounced anti-tumoral properties than 6-aza uracile, is generally effected by reaction of 6-aza uracile with a halogenated or acylated derivative of a sugar. In order to obtain ribosidation in a suitable position, that is to say at 1, it has been recommended (G.L. TONG, W.W. LEE. L. GOODMAN — J. Heterocyclic Chem 3 (2), 226-7 (1966)) to use, instead of 6-aza uracile, its trimethyl-silyl ether or di-3,5(trimethyl-siloxy) 1,2,4-triazine which is obtained by the action of hexamethyldisilazane $((CH_3)_3 Si)_2N$-H)in the presence of trimethyl-chlorosilane($(CH_3)_3$ SiCl)on 6-aza uracile.

The Applicants have found that, contrary to expectations, it was possible to carry out the cyclization of semi-carbazone of glyoxylic acid by heating with trialkylsilylation agents.

The silyl derivative of 6-aza uracile thus obtained can then be either isolated with a view to its utilization for subsequent syntheses or the 6-aza uracile can be obtained practically pure with a good yield by simple hydrolysis of the silyl derivative.

The overall reactions starting with sem-carbazone of glyoxylic acid may be written as follows when hexamethyldisilazane is used:

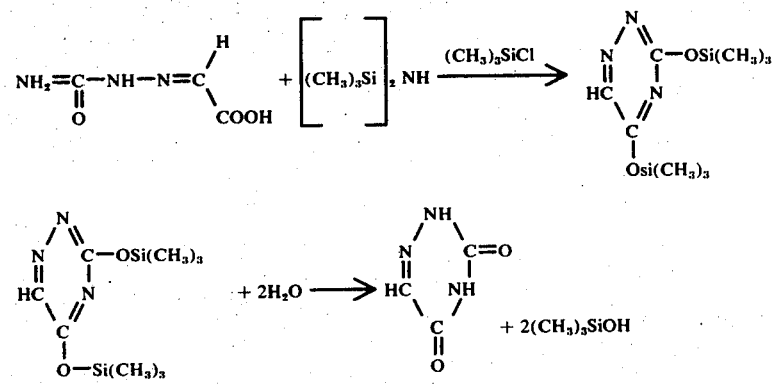

The semi-carbazone of glyoxylic acid may be prepared by the action of glyoxylic acid on semi-carbazide, or by any other appropriate method.

For the cyclization, all the trialkyl-silylation agents may be employed, especially the amino-trialkyl-silanes and the hexalkyl-disilazanes, the boiling point of which is higher than 120°C. in the presence of trimethyl-chloro-silane, such as triethylsilazane, trimethyl(butyl-amino)silane, triethyl(ethyl-amino)silane, trimethyl(-diethyl-amino)silane, trimethyl(dipropyl-amino)silane, triethyl(dimethyl-amino)silane, triethyl(diethyl-amino)silane, hexamethyl-disilazane, hexa-ethyl-disilazane and preferably those which comprise a trimethylsilyl group such as for example trimethyl(diethyl-amino)silane and hexamethyl-disilazane. It is also possible to utilize halogeno-trialkyl-silanes in the presence of ammonia or of an amine so as to form amino-trialkyl-silanes or hexa-alkyl-disilazanes in situ.

According to the invention, the cyclization is effected by heating semi-carbazone and trialkyl-silylation agent in excess, utilized as a solvent, in the presence of trimethyl-chloro-silane, to boiling point with reflux, and then for a very short time to a temperature higher than 150°C. for example, heating to boiling with reflux for several hours and then distilling the solvent at normal pressure until a temperature higher than 150°C. is obtained, or heating to boiling with reflux for about 30 minutes and then for a few minutes at a higher temperature, in the vicinity of 150°-160°C., after elimination of the solvent by distillation.

There is thus obtained the silyl derivative which may be utilized as it is for subsequent syntheses or may alternatively be hydrolyzed in order to obtain 6-aza uracile. The hydrolysis can readily be effected by simply treating the product with an aqueous acid solution, of acetic acid for example. Any other conventional hydrolysis method could obviously be employed.

The 6-aza uracile obtained is used in known manner as a medicament and in agriculture, and its silyl derivative is employed in the synthesis of medicaments.

The following examples will make the method of the invention more clearly understood, but they are in no way restrictive of the invention.

EXAMPLE 1

Into a reactor of 50 ml, there are introduced 1.5 grams of semi-carbazone of glyoxylic acid at 96.5 % and 10 grams of hexa-methyl-disilazane followed by a few drops of trimethyl-chloro-silane. The mixture is heated to boiling with reflux for 20 hours and then the solvent is distilled under normal pressure; the temperature reaches 160°C.

There is thus obtained a brownish oil which is the disilylated derivative of 6-aza uracile which is then hydrolyzed at ambient temperature by a 50 % aqueous solution of acetic acid (6 grams of acid at 100%). The precipitate which forms is filtered and dried; it weighs 1 gram. The NMR spectrum indicates that this precipitate is 6-aza uracile and that it contains no semi-carbazone. The yield is 80 percent.

EXAMPLE 2

The same quantities of reactants are heated as for the previous test, for 30 minutes at 130°C. and the solvent is then distilled under normal pressure. The temperature of the flask reaches 160°C. at the end of the distillation. The oil obtained (6.7 grams) is hydrolyzed as in example 1, and there is also obtained 1 gram of product which gives a yield of 80 percent.

EXAMPLE 3

A solution is prepared of trimethyl-(diethyl-amino) silane in xylene by causing 43.8 grams (0.6 mol) of diethyl-amine to react on 32.6 grams (0.3 mol) of trimethyl-chloro-silane for 2 hours at 60°C. and then separating the diethyl-amine hydrochloride. To the xylene solution obtained there are added 6.8 grams of semicarbazone of glyoxylic acid (0.05 mol) and 2 ml of trimethylchloro-silane. The mixture is heated to boiling with reflux for 30 minutes and the excess of reactant and solvent is distilled. The residual oil is brought up to 180°-190°C. and is then cooled and hydrolyzed with 27 grams of 50 % acetic acid. The precipitate which is formed is isolated and dried. This precipitate is 6-aza uracile with a weight of 2.5 grams, or a yield of 44 percent.

It will be understood that the present invention has been described only by way of explanation and not in any restrictive sense and that any useful modification may be made thereto without thereby departing from its scope as defined by the claims which follow.

We claim:
1. A method of preparation of 6-aza uracile, comprising the steps of:
  a. Cyclization of semi-carbazone of glyoxylic acid by heating this latter with an excess of a trialkyl-silylation agent taken as a solvent and isolating the resulting product, namely the O-disilylated derivative of 6-aza uracile (or di-3,5 (trialkylsiloxy)1,2,4 triazine) and
  b. subjection of the product resulting from step a) to an acid hydrolysis.

2. A method as claimed in claim 1, in which the trialkyl-silylation agent is selected from the amino-trialkyl-silanes and the hexa-alkyl-disilazanes, the boiling point of which is higher than 120°C. and the cyclization reaction is carried out in the presence of trimethyl-chloro-silane.

3. A method as claimed in claim 2, in which the amino-trialkylsilanes and the hexa-alkyl-disilazanes are selected from the group consisting in triethyl-silazane, trimethyl(butyl-amino)silane, triethyl(ethyl-amino)silane, trimethyl(diethyl-amino)silane, trimethyl(dipropyl-amino-silane) triethyl(dimethyl-amino)silane, triethyl(diethyl-amino)silane, hexamethyl-disilazane, hexa-ethyldisilazane, and preferably from those of these compounds which contain a trimethyl-silyl group.

4. A method as claimed in claim 1, in which the trialkylsilylation agent is constituted by a halogeno-trialkyl-silane and ammonia or an amine so as to form in situ an amino-trialkyl-silane or a hexa-alkyl-disilazane.

5. A method as claimed in claim 1, in which the step a) is carried out by heating the reactants to boiling with reflux and then for a very short time to a temperature higher than 150°C., after distillation of the solvent.

6. A method as claimed in claim 5, in which the reactants are heated to boiling with reflux for several hours and the solvent is then distilled at normal pressure until a temperature higher than 150°C. is obtained.

7. A method as claimed in claim 5, in which the reactants are heated to boiling with reflux for about 30 minutes, and then for a few minutes at a higher temperature in the vicinity of 150°-160°C., after elimination of the solvent by distillation.

8. A method as claimed in claim 1, in which the acid hydrolysis of the O-disilylated derivative is carried out in an aqueous solution.

9. A method as claimed in claim 8, in which the aqueous hydrolysis solution is a solution of acetic acid.

* * * * *